United States Patent [19]

Bloxom, Jr.

[11] Patent Number: 4,518,382

[45] Date of Patent: May 21, 1985

[54] APPARATUS FOR COLONIC AND INTESTINAL IRRIGATION

[76] Inventor: Ingrid B. Bloxom, Jr., P.O. Box 357, Wicomoco, Va. 23184

[21] Appl. No.: 556,036

[22] Filed: Nov. 29, 1983

[51] Int. Cl.³ .............................................. A61M 1/00
[52] U.S. Cl. ..................................... 604/27; 604/48; 604/73; 604/257
[58] Field of Search ...................... 604/27, 29, 30-34, 604/48, 54, 73, 80, 246, 257, 277; 116/273; 33/370, 371, 365

[56] References Cited

U.S. PATENT DOCUMENTS

| 1,227,842 | 5/1917 | Sellin | 116/273 |
| 2,067,474 | 1/1937 | Carbonara | 33/365 |
| 2,257,072 | 9/1941 | Coombs | 604/35 |
| 2,847,969 | 8/1958 | Woodruff | 116/273 |
| 4,435,171 | 3/1984 | Goldberg et al. | 604/49 |

FOREIGN PATENT DOCUMENTS 2754809  6/1979  Fed. Rep. of Germany ........ 604/27

Primary Examiner—C. Fred Rosenbaum
Assistant Examiner—J. L. Kruter
Attorney, Agent, or Firm—John Cyril Malloy

[57] ABSTRACT

Apparatus for accomplishing irrigation of the colon and/or other intestinal portions through a stoma including an established path of fluid flow of irrigating liquid from a supply container through a feeding tube into a stoma cone or like structure and further including a peristaltic action monitoring device disposed within the path of fluid flow of irrigating fluid which is structured to indicate, through visual observation, the establishment of peristaltic action in the intestine which tends to reverse the direction of flow of the irrigating fluid and provides proper indication when the flow of the irrigating fluid to the intestine or colon should be stopped.

6 Claims, 4 Drawing Figures

APPARATUS FOR COLONIC AND INTESTINAL IRRIGATION

BACKGROUND OF THE INVENTION

Colonic irrigation is a well known medical treatment, not only in the case of conventional enemas through the anus end of the rectum, but also in the case of irrigation through surgically provided openings into other parts of the colon, as in the case of colostomy and ileostomy patients. In all of these cases the degree of discomfort and length of the ordeal is significant. Although varying in particular cases, it is particularly disagreeable for those requiring irrigation directly into the colon through surgically provided stoma. Such stomas are formed from the end of a shortened colon after the end has been drawn up through the stomach wall and outer skin.

Equipment to introduce irrigation liquid into the colon of an ostomy patient is disclosed, for example, in U.S. Pat. No. 3,830,235 of Marsan. Such equipment conventionally includes a bag for the irrigation liquid, a flexible tube to convey the liquid from the bag to a stoma cone through which the liquid is introduced into the colon, a clip to shut off the flow to the tube, and a discharge device to catch the backflow when the cone is removed from the stoma. The irrigation liquid is conventionally water, or water with soap or other agents. Such agents are disclosed, for example, in U.S. Pat. No. 4,052,986 of Scaife.

SUMMARY OF THE INVENTION

In accordance with the present invention, the discomfort and time required for colonic or other intestinal irrigation is minimized by detecting the buildup of peristaltic action of the intestine in response to injection of irrigation liquid, and terminating the injection when there is an indication of sufficient peristaltic action to provide the desired evacuation without the aid of additional fluid. Such prompt termination has the further important advantage of preventing an excessively large injection of fluid from suppressing the peristaltic action initiated by the smaller amount of fluid initially injected. When injections are made in accordance with the invention, injection of about half a pint or less is usually enough, and it is best not to exceed one pint before terminating further injection and taking a laxative preliminary to renewing the injection the next day. Conventional irrigations, on the other hand, usually call for injection of one or two quarts of liquid, which suppresses peristaltic action and tends to prolong the period of evacuation afterwards, as well as taking longer to administer and greatly adding to the discomfort of the patient.

In the present preferred practice of the invention, a mechanical indicator of peristaltic action is mounted in the tube which conveys liquid to the cone inserted in the stoma of the patient. This indicator is preferably in the form of a horizontally extending transparent tube containing a ball which is readily moveable between the ends of the tube, with enough clearance in all positions of the ball to permit the fluid to pass in either direction through the sighting tube. Peristolic action in the intestine tend to move fluid in the opposite direction to that of the fluid being injected, and the pulsing effects of the peristaltic action causes the ball to move in a fluctuating manner in a direction opposite to the flow of irrigating fluid toward the stoma cone. As this fluctuation builds up the ball moves all the way to the end of the sighting tube connected to the source of the irrigation liquid, and that is when enough peristaltic action has been developed to indicate that further irrigation should be terminated. Alternatively, electrical equipment like that used to detect the action of heart muscles for making electrocardiograms may be used to detect the action of the muscles which produce peristaltic action, and the signals thus obtained may be used to generate visible indications of peristaltic action useful for determining when irrigation should be terminated.

The invention further makes it possible to make the most effective use of additives for increasing the effect of the water in stimulating peristaltic action and softening or breaking up feces in the intestine being irrigated. In the practice of the invention the most useful of these agents is linear dodecylbenzenesulfonate sodium salt, preferably used in proportions by volume of one part of water to 0.008 parts of this agent. Through use of this agent the amount of water may be reduced by about one third, thus reducing the time required for the injection.

These and other features, advantages and details of the invention will become apparent as the following description proceeds.

BRIEF DESCRIPTION OF THE DRAWINGS

The accompanying drawings schematically illustrate present preferred apparatus of the invention, as follows.

DETAILED DESCRIPTION OF PRESENT PREFERRED EMBODIMENTS AND PRACTICE OF THE INVENTION

Figure 1:
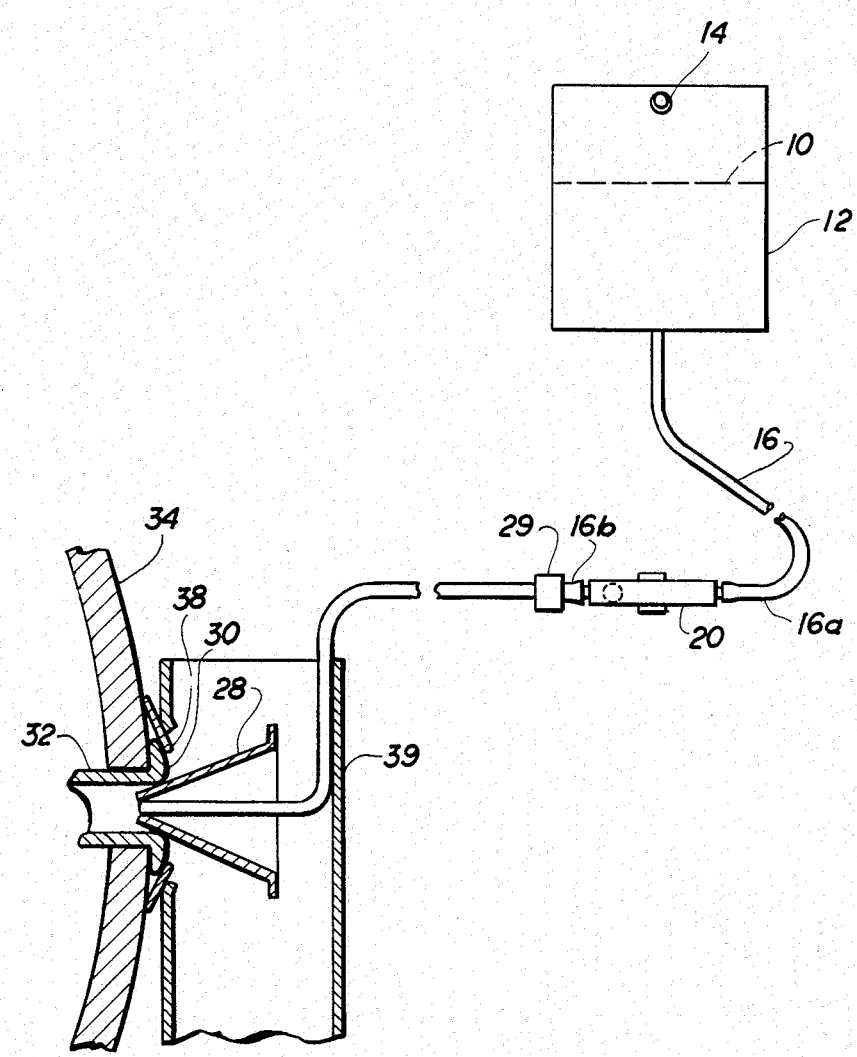
FIG. 1 shows a side view, partially broken away and sectioned, of an irrigational liquid supply bag, a tube feeding through an indicating device of the invention to a stoma and body wall through a stoma cone, with discharge sleeve.
Figure 2:
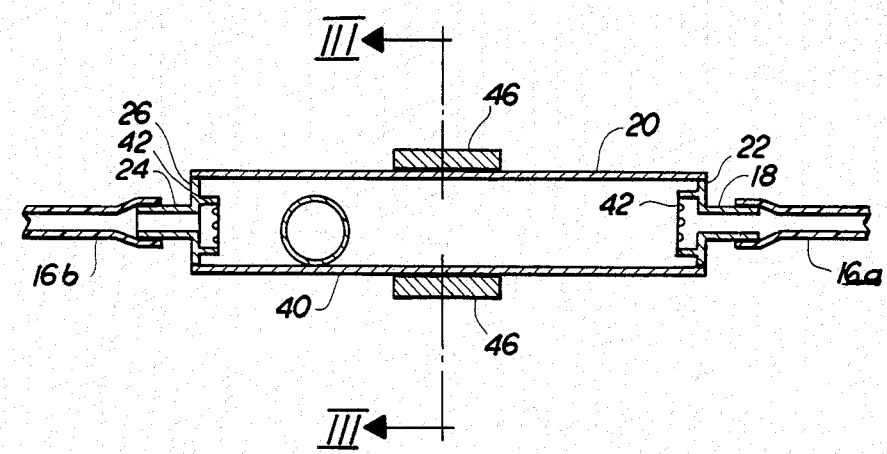
FIG. 2 shows an enlarged view of the indicator of the invention and adjacent ends of the connected tube, in vertical section through the central axis of the indicator.

Referring now more particularly to the drawings, and initially to FIG. 1, a bag 10 containing irrigation liquid 12 is suspended by a fixed hook 14, and has a bottom outlet connected to a supply tube 16 of flexible plastic material. The tube 16 has one portion 16a connected at one end to the outlet of container 10, and at its other end is connected to a nozzle 18 projecting from one end of a hollow cylinder 20. (see FIG. 2) An end wall 22 closes the space between the base of the nozzle 18 and adjacent end of cylinder 20. A similar nozzle 24 on the end wall 26 is positioned at the other end of cylinder 20, and is connected to one end of portion 16b of the tube 16. The other end of tube portion 16b is inserted into and frictionally held by the converging interior of a flexible plastic cone 28. (FIG. 1)

The cone 28 is made conventionally for insertion into a stoma 30 at the end of a length of intestine 32 extending through the outer body wall 34 of a patient. Preliminary to insertion of the stoma it is conventional to secure a plastic sleeve 36 to the outside of the body wall 34, with a side opening through the sleeve 39 surrounding and radially spaced from the stoma 30. The margin of the opening through sleeve 39 is secured to a relatively stiff but flexible retaining member 38, which has an opening through it positioned around the stoma 30, and which has side extensions (not shown) attached to belt straps (not shown) going around the patient's waist to hold the member 38 and sleeve 39 in place. When the sleeve 39 is in place, the cone 28 with attached tube portion 16b can be passed down through the upper end of sleeve 39 for insertion into the stoma.

A conventional squeeze valve 29 is secured around tube 16 at any convenient position where it may be operated to permit or shut off flow of liquid through tube 16.

The cylinder 20 is made of transparent material, such as plastic, in order to permit inspection of a ball 40 contained within and freely moveable lengthwise along the cylinder. Movement and position of the ball provides a visual indication of direction of flow through the cylinder 20 and connected supply tube 16. Means such as crenallated rings 42 are mounted inside the end walls 22 and 26 around the passageways into the nozzles 18 and 24, in order to prevent ball 40 from blocking normal flow of fluid when it reaches the end of cylinder 20. Similarly, ball 40 is of enough smaller outer diameter than the inner diameter cylinder 20 to provide enough clearance for normal flow of liquid between the ball and the inside of the cylinder 20.

The cylinder 20 should be held horizontally so that the ball 40 will be free of any gravitational force tending to move it one way or the other. A clip 44 with holding arms 46 is provided for this purpose. A bolt 48 secures the clip 44 to a base 50 adapted to be mounted in a vertical position. The base 50 may be secured permanently, or may be in the form of a board adapted to be suspended at its ends from a curtain rod. When the base 50 is in its vertical position, the bolt 48 extends horizontally and the clip 44 may be rotated around the bolt 48 relative to the base 50 until cylinder 20 is in the desired horizontal alignment.

Figure 4:
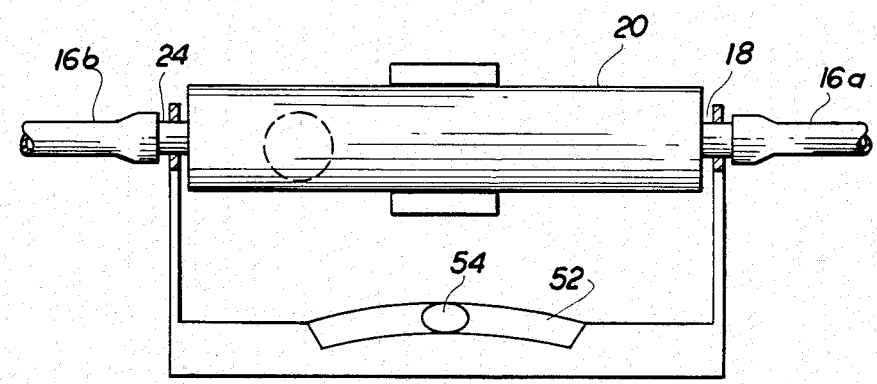
FIG. 4 shows a view corresponding to FIG. 3, but unsectioned and including an attached signt level gauge.
Figure 3:
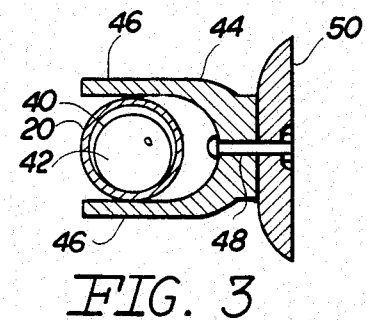
FIG. 3 shows a section on the line III—III in FIG. 2.

When cylinder 20 is initially filled with liquid received from tube portion 16a, some of the air initially in cylinder 20 remains in it and can be reduced to a relatively small bubble. This bubble can be observed in the manner of a level gauge for purposes of adjusting the position of cylinder 20 accurately. Alternatively, as illustrated in FIG. 4, a conventional level gauge 52 with bubble 54 may be suspended beneath cylinder 20 by arms hooked around nozzles 18 and 24, in proper alignment to indicate accurately when cylinder 20 is horizontal.

For best results, the ball 40 should have a little higher specific gravity than the irrigation liquid, and should have a diameter of at least two thirds the inside diameter of cylinder 20. For example, successfully used apparatus employed a cylinder having an inside diameter of substantially 9/16 inch and a hollow metal ball having an outside diameter of substantially 7/16 inch. The ball had been made for a string of beads and hence was pierced and had a decorative knurled outer surface. The length of free travel of the ball in the cylinder was substantially 3¼ inches. The inside diameter of the nozzles 18 and 24 are substantially 3/16 inch, and the inside diameter of the tube portions 16a and 16b was substantially ⅛ inch. The bag 14 is preferably mounted on a level such that the bottom of the bag 10 is about at eye level of the person using the apparatus, if self administered. The sighting cylinder 20 is preferably mounted about two feet below the top of the bag. It has been found convenient, for example, to mount a two foot vertical bar (not shown) in a permanent position suitable for the purposes of the disclosed apparatus, with the hook 14 mounted at the top of the bar and the clip 44 mounted at the bottom of the bar.

In using the apparatus, ball 40 moves toward nozzle 24 as the supply of irrigating liquid begins. As irrigation continues peristaltic action of the colon is stimulated and begins to build up. Since this action tends to move the colon contents toward the stoma, the result is waves of resistance to inflow from tube 16, until the peristaltic action builds up to a point where it causes waves of backflow through tube 16. While this is going on, ball 40 is observed to fluctuate back and forth until it finally moves to the end of cylinder 20 connected to nozzle 18. At that point there has been a sufficient build up of peristaltic action, and a shut-off valve 29 is operated to stop further flow through tube 16 in either direction. Cone 28 is then removed from stoma 30, and normal evacuation through stoma 30 will proceed in a few minutes. Excess fluid in bag 12 can be used to wash out the interior of sleeve 39. This can usually be done in 10 to 20 minutes, as a general rule, and rarely as much as 30 minutes are required. The process encourages normal peristaltic action, and hence it is only necessary to use it on a twice a week basis.

If the ball has not moved to the nozzle 18 end of cylinder 20 by the time a pint of liquid has been injected, the patient should terminate the procedure and use laxative medicine before continuing the procedure the next day. Ordinarily, however, only about half a pint of liquid will be required.

Plain water works very well for purposes of the invention. However, its action may usefully be accelerated by adding to the water a supply of linear dodecylbenzenesulfonate sodium salt in a ratio by volume of one part of water to 0.008 parts of this additive. This may be accomplished, for example, by using three-quarters of an ounce of liquid dishwashing composition sold by Amway Corporation under the trademark "Dish Drops", in two quarts of water. The effectiveness of this addition, which is a surface active agent, is to accelerate the action of water in stimulating peristaltic action and softening or breaking up feces. Only about 8 to 10 ounces of water with this addition ordinarily need to be injected during each twice a week treatment. Only after 2 ounces of liquid have been injected through the stoma should monitoring of sighting cylinder 20 begin. About half again more water and more time is ordinarily required without the additive.

What has been disclosed above with reference to injection through a stoma generally applies to injection through an anus, except that a modified cone is used with a tube about ¾ inch long to go past and prevent closure by the sphincter muscle.

Suitable indication of peristaltic action for purposes of the invention can alternatively be obtained by monitoring the electro signals of the muscles which give rise to the peristaltic action by electrical equipment corresponding to that used to make electrocardiograms.

While present preferred embodiments and methods of practicing the invention have been illustrated and described, it will be understood that the invention may be otherwise variously embodied and practiced within the scope of the following claims.

I claim:

1. An apparatus for controlled intestinal irrigation comprising:

(a) a container means for supply and storage of irrigating liquid,
(b) introduction means positionable adjacent to and in fluid delivering relation with an entrance to an intestine being irrigated for introducing liquid thereto,
(c) conduit means disposed in interconnecting and fluid communicating relation between said container means and said introduction means,
(d) flow regulating means connected to said conduit means and structured and disposed to stop and control liquid flow from said container means to said introduction means, whereby flow of irrigating fluid to the intestine is selectively stopped by said flow regulating means upon an indication of peristaltic action of the intestine by a flow indicator,
(e) a flow indicator means connected to said conduit means between said container means and said introduction means and structured to accommodate liquid flow therethrough from said container means to the intestine and reversely from the intestine into said flow indicator means,
(f) said flow indicator means first structured for visual observation of at least a portion of the interior thereof and including an indicator element movably disposed therein and within liquid flow passing therethrough,
(g) said indicator element cooperatively structured and disposed relative to said flow indicator means for responsive displacement therein based on peristaltic action of the intestine during flow of liquid through said flow indicator means to the intestine.

2. An apparatus as in claim 1 wherein said flow indicator means comprises a tube having a transparent wall portion and connected at opposite ends thereof to the conduit means for direction of liquid through said tube, said indicator element visible through said transparent wall portion and movable between opposite ends of said tube without preventing liquid flow through said tube in either direction, and said indicator element being movable toward one opposite end of said tube in response to liquid flow therethrough from said container means and movable towards the other of said opposite ends of said tube against the liquid flow from said container in response to peristaltic activity of the intestine.

3. An apparatus as in claim 2 comprising a level gauge secured to said tube for indication when said tube is in a horizontal orientation.

4. An apparatus as in claim 1 wherein said indicator element is a ball and said tube has a cylindrical interior of greater cross-sectional diameter than the diameter of said ball.

5. An apparatus as in claim 4 wherein said ball has a specific gravity greater than that of water.

6. An apparatus as in claim 1 further including holding means to hold said tube and securing means to attach said holding means to a fixed support, said holding means and securing means being relatively rotatable, and said holding means rotatable relative to said fixed support until said tube is in a horizontal position.

* * * * *